United States Patent

Minagawa et al.

[11] Patent Number: 4,469,828
[45] Date of Patent: Sep. 4, 1984

[54] ALKYLTHIOPROPIONYL HYDRAZINO TRIAZINES AND SYNTHETIC RESIN COMPOSITIONS

[75] Inventors: Motonobu Minagawa, Koshigaya; Tohru Haruna, Okegawa; Masayuki Takahashi, Tokorozawa, all of Japan

[73] Assignee: Adeka Argus Chemical Co., Ltd., Urawa, Japan

[21] Appl. No.: 443,363

[22] Filed: Nov. 22, 1982

[51] Int. Cl.³ ............... C07D 251/00; C07D 251/18; C07D 403/00; C08K 5/34
[52] U.S. Cl. ............................ 524/100; 544/196; 544/198; 544/204; 544/209; 544/210; 544/213; 544/219
[58] Field of Search ............ 524/191, 100; 544/196, 544/198, 204, 209, 210, 213, 219

[56] References Cited

U.S. PATENT DOCUMENTS 3,509,093 4/1970 Lehmann et al. .................. 524/191
4,263,434 4/1981 Cassandrini et al. ............... 524/100

Primary Examiner—John Kight, III
Assistant Examiner—Kriellion Morgan

[57] ABSTRACT

Alkylthiopropionyl hydrazino triazines are provided having the formula:

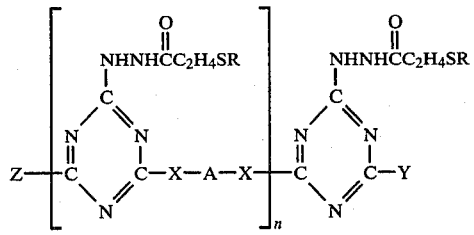

wherein:
R is alkyl having from one to about fifty carbon atoms;
X is

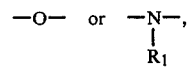

where $R_1$ is selected from the group consisting of hydrogen, alkyl having from one to about fifty carbon atoms; and

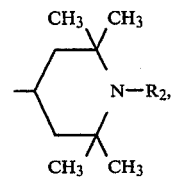

where $R_2$ is selected from the group consisting of hydrogen, O and alkyl hydroxyalkyl, epoxy alkyl and acyloxy alkyl having from one or two to about eight carbon atoms;
when X is O, A is selected from the group consisting of alkylene having from two to about twenty carbon atoms, cycloalkylene having from about five to about eight carbon atoms and phenylene;
when X is

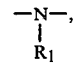

A is selected from the group consisting of a direct linkage, alkylene having from one to about twenty carbon atoms, cycloalkylene having from five to about eight carbon atoms; phenylene; and

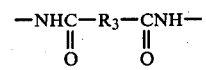

where $R_3$ is a direct linkage, alkylene having from one to about twenty carbon atoms; cycloalkylene having from about five to about eight carbon atoms; phenylene; and thiodialkylene having from about two to about twenty carbon atoms.

24 Claims, No Drawings

ALKYLTHIOPROPIONYL HYDRAZINO TRIAZINES AND SYNTHETIC RESIN COMPOSITIONS

Polymers such as polyethylene, polypropylene, ABS resin, etc. are subject to degradation upon heating, with accompanying discoloration and deterioration of mechanical strength. Various stabilizers have been used to inhibit heat deterioration. Thioether compounds such as dialkyl thiodipropionates act as a hydroperoxide decomposers, and have a synergistic stabilizing effect with phenolic antioxidants. However, the conventional thioether compounds are generally unsatisfactory in their stabilizing effect, and some of them are heat-unstable, and decompose and volatilize when heated during processing.

For example, the dialkyl thiodipropionates such as dilauryl thiodipropionate leave much to be desired in their stabilizing effect, particularly at high temperatures while the alkylthiopropionic acid hydrazides are uncompatible and give Nise to bloom, while their stabilizing effect also is unsatisfactory.

In accordance with the present invention, alkyl thiopropionyl hydrozino triazines are provided having the formula:

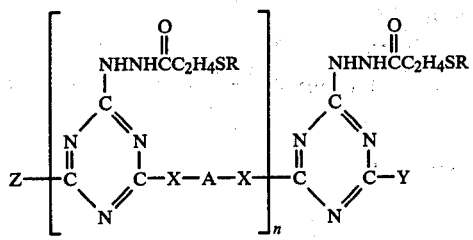

wherein:
R is alkyl having from one to about fifty carbon atoms;
X is

-O- or 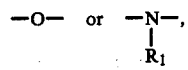

where $R_1$ is selected from the group consisting of hydrogen, alkyl having from one to about fifty carbon atoms; and

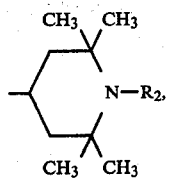

where $R_2$ is selected from the group consisting of hydrogen, O and alkyl hydroxyalkyl, epoxy alkyl and acyloxy alkyl having from one or two to about eight carbon atoms;

when X is O, A is selected from the group consisting of alkylene having from two to about twenty carbon atoms, cycloalkylene having from about five to about eight carbon atoms and phenylene;
when X is

A is selected from the group consisting of a direct linkage, alkylene having from one to about twenty carbon atoms, cycloalkylene having from five to about eight carbon atoms; phenylene; and

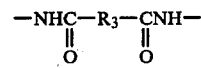

where $R_3$ is a direct linkage, alkylene having from one to about twenty carbon atoms; cycloalkylene having from about five to about eight carbon atoms; phenylene; and thiodialkylene having from about two to about twenty carbon atoms;

Y and Z are each selected from the group consisting of

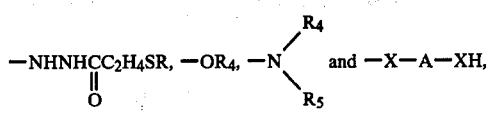

where $R_4$ and $R_5$ each are selected from the group consisting of hydrogen; alkyl having from one to about fifty carbon atoms, cycloalkyl having from about five to about eight carbon atoms; phenyl; and alkyl phenyl having from seven to about twenty carbon atoms; and

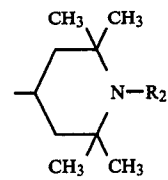

n is a number from 0 to about 20.

Also in accordance with the invention, synthetic resin compositions are provided having an improved resistance to deterioration when heated, comprising synthetic resin and a stability-enhancing amount of one or more of such alkyl thiodipropionyl hydrazinyl triazines.

Exemplary R, $R_1$, $R_4$ and $R_5$ alkyl include methyl, ethyl, propyl, isopropyl, butyl, isobutyl, tert-butyl, hexyl, octyl, isooctyl, 2-ethylhexyl, decyl, undecyl, dodecyl, tetradecyl, hexadecyl, octadecyl, eicosyl, docosyl, tetracosyl, triacontyl, tetracontyl and pentacontyl.

Exemplary R, $R_1$, $R_4$ and $R_5$ cycloalkyl include cyclopentyl, cyclohexyl, cycloheptyl and cyclooctyl.

Exemplary $R_2$ groups include methyl, ethyl, propyl, isopropyl, butyl, isobutyl, tert-butyl, octyl, isooctyl, 2-ethylhexyl, hydroxyethyl, hydroxypropyl, hydroxybutyl, hydroxyoctyl, acetoxyethyl, acetoxypropyl, propionoxypropyl, butyroxybutyl, butyroxyethyl, 1,2-epoxypropyl, 2,3-epoxy butyl, 1,2-epoxy butyl, 1,2-epoxy hexyl, 3,4-epoxy octyl, 1,2-epoxy octyl.

Exemplary A and $R_3$ alkylene are methylene, ethylene, 1,3-propylene, 1,2-propylene, 1,4-butylene, neopentylene, hexamethylene, octamethylene, decamethylene, undecamethylene, dodecamethylene, hexadecamethylene, octadecamethylene and eicosamethylene
Exemplary A and $R_3$ cycloalkylene include cyclopentylene, cyclohexylene, cycloheptylene and cyclooctylene.
Exemplary $R_4$ alkyl phenyl include tolyl, xylyl, ethyl phenyl, diethyl phenyl, butyl phenyl, dibutyl phenyl, and diheptyl phenyl.
Examples of compounds of the invention are:
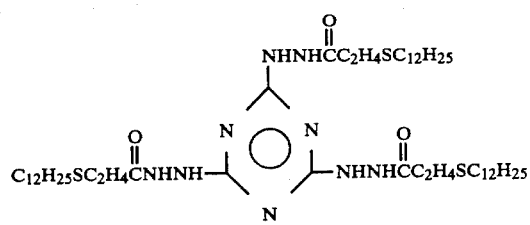
1.
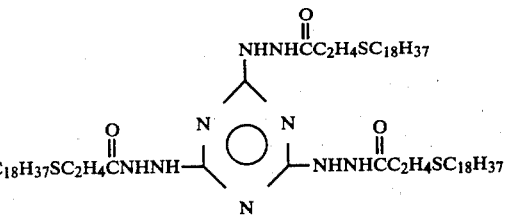
2.
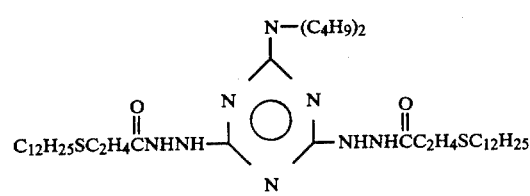
3.
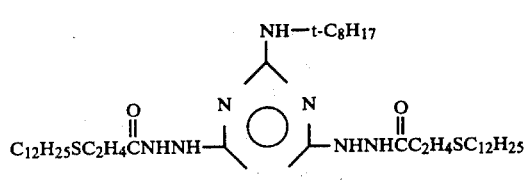
4.
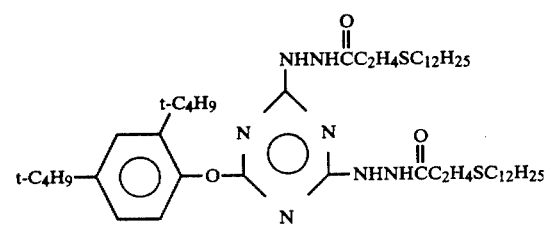
5.
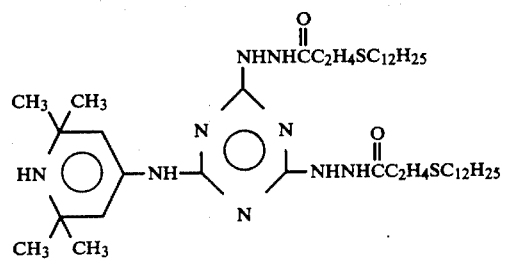
6.
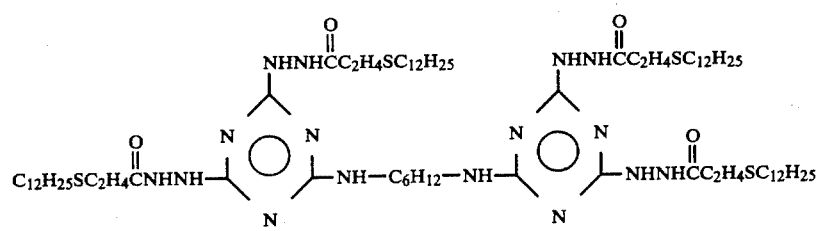
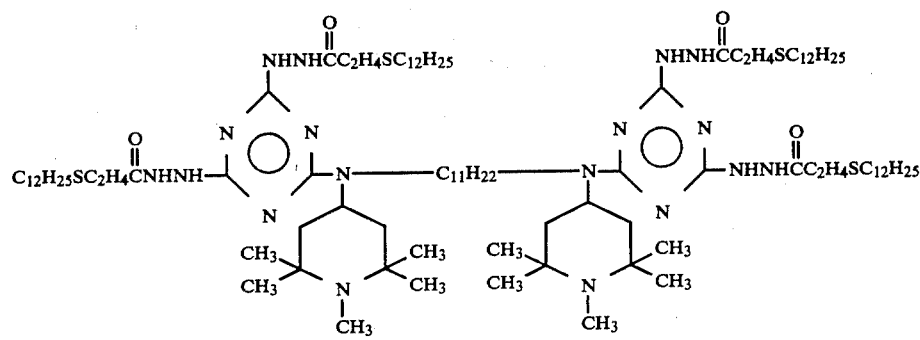
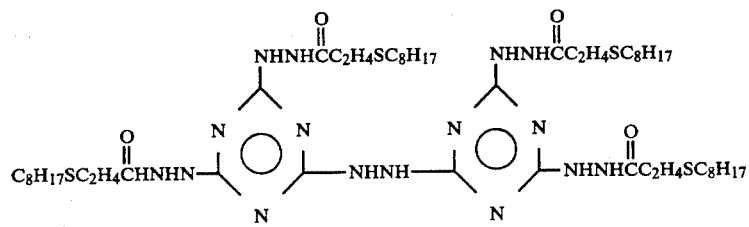

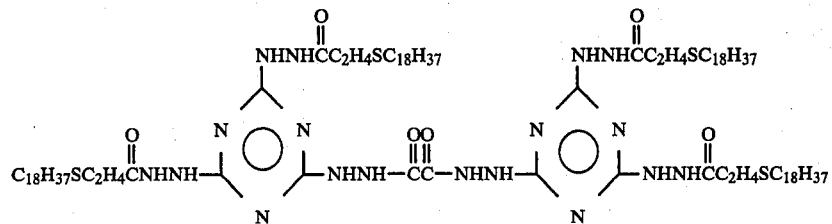
10.
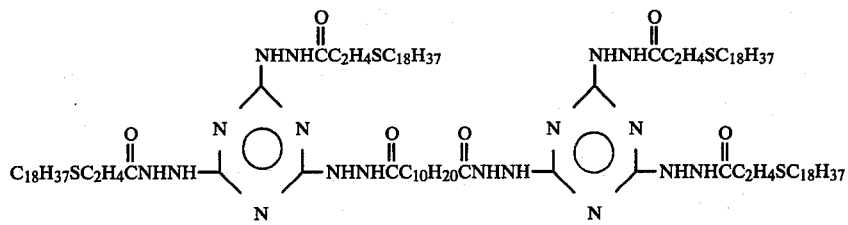
11.
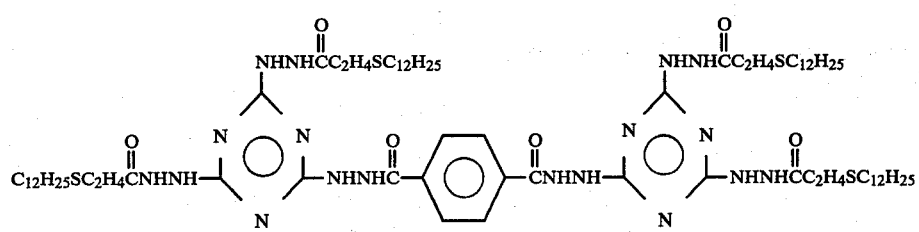
12.
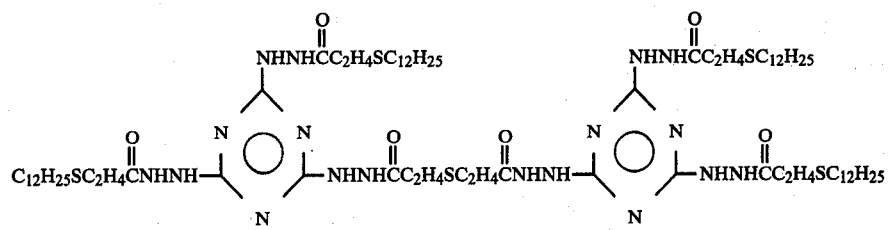
13.
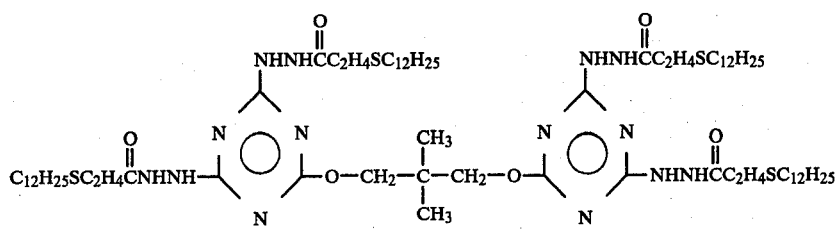
14.
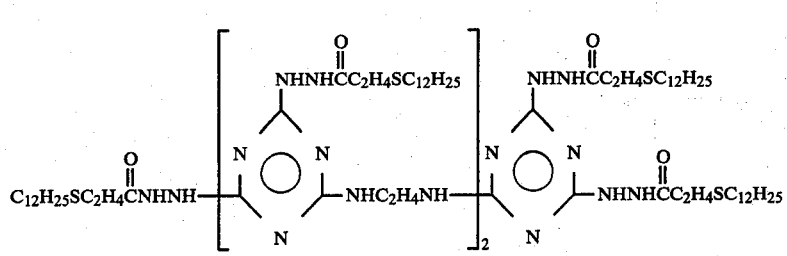
15.
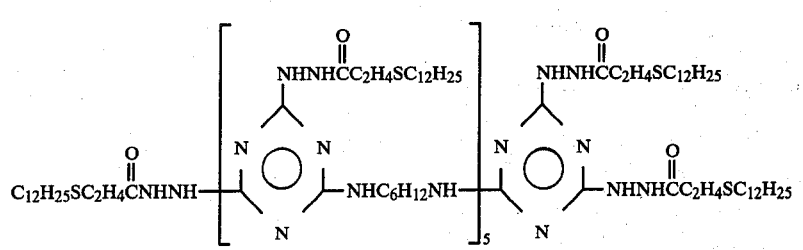
16.

-continued
17.
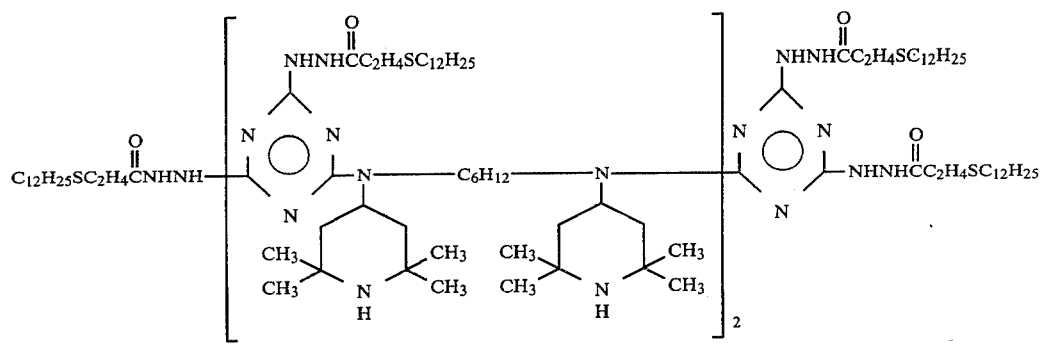
18.
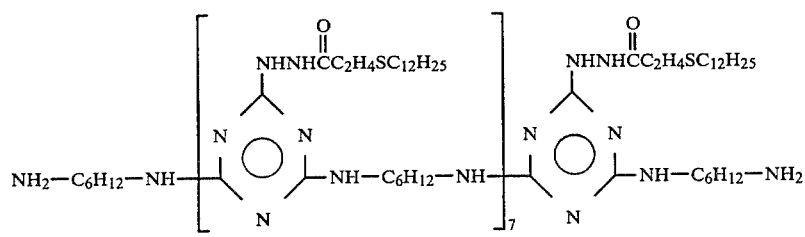
19.
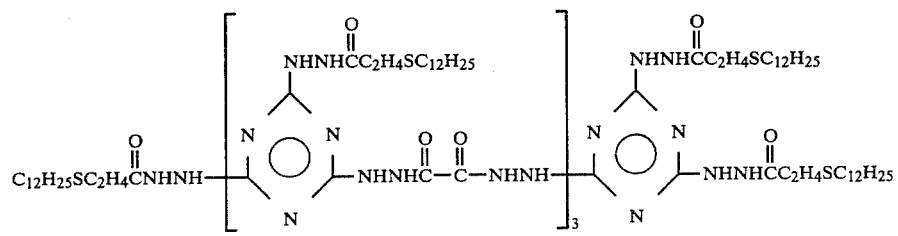
20.
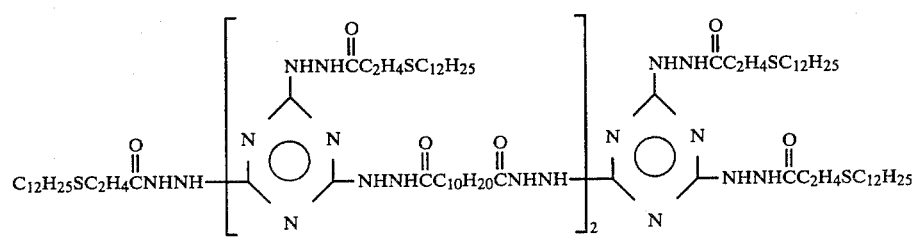
21.
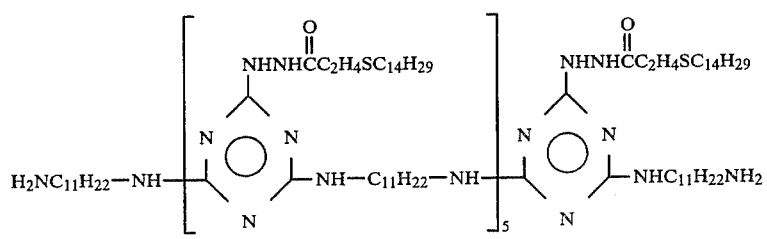
22.
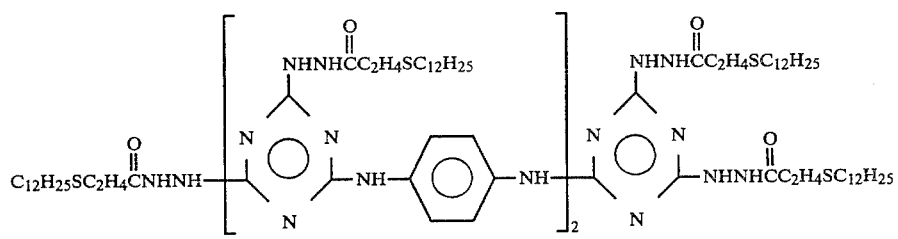
The compounds of the invention can be prepared by the reaction of cyanuric chloride with the corresponding alkylthiopropionic acid hydrazide and any corresponding amines, alcohols or phenols according to A, X, Y and Z.

The following synthetic Examples illustrate preferred embodiments of the preparation of the compounds listed above.

EXAMPLE A

Preparation of

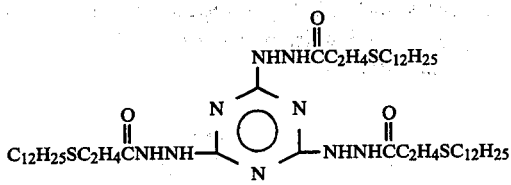

Cyanuric chloride 3.69 g and dodecylthiopropionic acid hydrazide 17.9 g were dissolved in 50 ml of dimethylacetamide and stirred at 45° to 50° C. for one hour. A solution of 4.9 g of pyridine and 20 ml of dimethylacetamide was then added at 60° C. over 20 minutes. The resulting solution was stirred at 80° C. for 5 hours, and cooled to room temperature. The solution was poured into 500 ml of water, and the precipitated powder filtered. The product was recrystallized from methyl cellosolve/dimethylacetamide (1:1). 18.5 g of white powder, melting at 210° to 215° C., was obtained.

EXAMPLE B

Preparation of

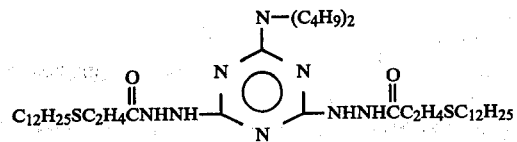

2-(Di-n-butylamino)-4,6-dichloro-s-triazine 5.54 g and dodecylthiopropionic acid hydrazide 5.76 g were dissolved in 50 ml of dimethylacetamide, and stirred at 15° to 20° C. while adding 40% aqueous NaOH solution over 10 minutes. The solution was stirred for 30 minutes, then heated to 45° C. and stirred for 4.5 hours. 5.76 g of dodecyl thiopropionic acid hydrazide and 2.1 g of 40% aqueous NaOH solution was added, and the reaction mixture stirred at 85° C. for 4.5 hours. The precipitated sodium chloride were filtered, and the filtrate was poured into 500 ml of water. The precipitated powder was filtered and recrystallized from methyl cellosolve. 14.0 g of white powder, melting at 200° to 205° C., was obtained.

The alkyl thiopropionyl hydrazino triazines of this invention can be added to synthetic resins to stabilize the resin in an amount to enhance the resistance of the resin to deterioration when heated and when exposed to air and light within the range from about 0.001 to about 5, preferably from about 0.01 to about 3, parts by weight per 100 parts by weight of resin.

The compounds of this invention serve not only as antioxidants for synthetic resins but also as metal deactivators. The alkyl thiopropionyl hydrazino triazines of this invention also improve resistance to deterioration of synthetic resin compositions filled with conventional filters such as talc, calcium carbonate, barium sulfate and asbestos.

Although dialkylthiodipropionates show an antagonistic or depreciating effect when used in combinations with 2,2,6,6-tetramethylpiperidine light stabilizers, the alkyl thiopropionyl hydrazino triazines of this invention synergize the effect of 2,2,6,6-tetramethyl piperidines, rather than decrease the effect.

Examples of 2,2,6,6-tetramethylpiperidine compounds that can be used in such synergistic combinations are 2,2,6,6-tetramethyl-4-piperidinyl benzoate, N-hydroxy ethyl-2,2,6,6-tetramethyl-4-piperidinyl-bis(3,5-di-t-butyl-4-hydroxyphenyl-propionate), bis(2,2,6,6-tetramethyl-4-piperidinyl)sebacate, bis(1,2,2,6,6-pentamethyl-4-piperidinyl) sebacate, bis(1,2,2,6,6-pentamethyl-4-piperidinyl)-2-n-butyl-2-(3,5-di-t-butyl-4-hydroxybenzyl) malonate, tris(2,2,6,6-tetramethyl-4-piperidinyl) nitrilo triacetate, tetrakis (2,2,6,6-tetramethyl-4-piperidinyl)-1,2,3,4-butanetetracarboxylate, the condensation product of N-hydroxyethyl-2,2,6,6-tetramethyl-4-piperidinol with dimethyl succinate, bis(9-aza-8,8,10,10- tetramethyl-3-ethyl-1,5-dioxaspiro[5,5]-3-undecylmethyl-oxycarbonyloxy)-4,4'-isopropylidenbiscyclohexane, bis(9-aza-8,8,10,10-tetramethyl-3-hydroxymethyl-1,5-dioxaspiro[5,5]-3-undecyl methylether and the condensation product of cyanuric chloride, t-octylamine and bis(2,2,6,6-tetramethyl-4-piperidinyl amino) hexane.

Synthetic resins that can have their resistance to deterioration enhanced with alkyl thiopropionyl hydrazino triazines according to this invention include α-olefin polymers such as polyethylene, polypropylene, polybutene, poly-3-methylbutene, or mixtures thereof, and copolymers with other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer; acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The alkyl thiopropionyl hydrazino triazines of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In case of the bicyclic phenols, the rings can be linked by thio or oxyether groups, or by alkylene, alicyclidene or arylidene groups.

The monocyclic phenols which can be employed have the structure:

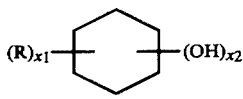

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

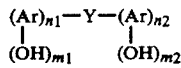

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

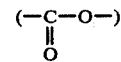

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

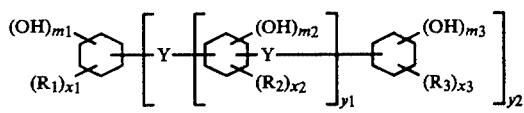

wherein $R_1$, $R_2$ and $R_3$ are inert substituent groups as described in the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

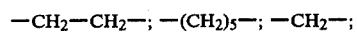

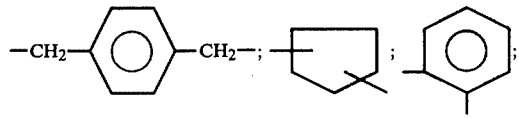

(2) Y groups where only atoms other than carbon link the aromatic rings, such as $-O-$, $-S-$, $-\underset{O}{\overset{O}{S}}-$, $-\underset{O}{\overset{O}{S}}-$ and $-(S)_x-$ where x is a number from one to ten;

(3) Y groups made up of more than a single atom including both carbon and other atoms linking the aromatic nuclei, such as:

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxyphenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl (4-hydroxy-3-methyl-5-t-butyl)benzylmalonate.

Exemplary polyhydric phenols are orcinol, propyl gallate, catechol, resorcinol, 4-octyl-resorcinol, 4-dodecyl-resorcinol, 4-octadecyl-catechol, 4-isooctyl-phloroglucinol, pyrogallol, hexahydroxybenzene, 4-isohexyl-catechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis (2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol, 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)-phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis (naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl)propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenyl), (3,5-di-tert-butyl-4-hydroxyphenyl)-(4'-hydroxyphenyl)ethane, (2-hydroxyphenyl)-(3',5'-di-tert-butyl-4',4-hydroxyphenyl)ethane, 2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5- triazine, 2,4,6-tris-(4-hydroxy-3-t-butyl-phenoxy)-;b 1,3,5-triazine, 2,2'-bis-(3-t-butyl-4-hydroxyphenyl) thiazolo-(5,4-d) thiazole, 2,2'-bis-(3-methyl-5-t-butyl-4-hydroxyphenyl) thiazolo-(5,4-d)-thiazole, 4,4'-bis-(4-hydroxyphenyl) pentanoic acid octadecyl ester, cyclopentylene-4,4'-bis-phenol, 2-ethyl-butylene-4,4'-bisphenol, 4,4'-cycloctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl) sulfide, bis-(2-tert-butyl-4-hydroxy-5-methylphenyl) sulfide, bis-(2-tert-butyl-4-hydroxy-5-methylphenyl)sulfoxide, bis-(3-ethyl-5-tert-butyl-4-hydroxyphenyl) sulfide, bis-(2-hydroxy-4- methyl-6-tert-butylphenyl) sulfide, 4,4'-bis-(4- hydroxyphenol) pentanoic acid octadecyl thiopropionate ester, 1,1,3-tris-(2'-methyl-4- hydroxy-5'-tert- butylphenyl) butane,1,1,3-tris-(1-methyl-3-hydroxy-4-tert-butylphenyl) butane, 1,8-bis-(2-hydroxy-b 5- methylbenzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl-naphthalene, 2,2'-(2-butene)-bis-(4-methoxy-6-tert-butylphenol)-bis-[3,3-bis-(4-hydroxy-3-t-butylphenyl) butyric acid] glycol ester, 4,4'-butylidene-bis-(6-t-butyl-m-cresol), 1,1,3-tris-(2-methyl-4-hydroxy-5-t-butylphenyl) butane, 1,3,5-tris-(3,5-di-t-butyl-4-hydroxybenzyl)-2,4,6-trimethylbenzene, tetrakis [methylene-3(3,5-di-t-butyl-4-hydroxyphenyl)propionate] methane, 1,3,5-tris-(3,5-di-t-butyl-4-hydroxybenzyl) isocyanurate, 1,3,5-tris-(3,5-di-t- butyl-4-hydroxyphenyl) propionyloxyethyl isocyannurate, 2-octylthio-4,6-di-(4-hydroxy-3,5-di-t-butyl) phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

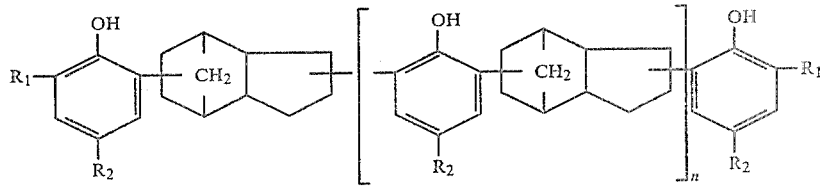

in which

R₁ and R₂ are lower alkyl, and can be the same or different, and n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

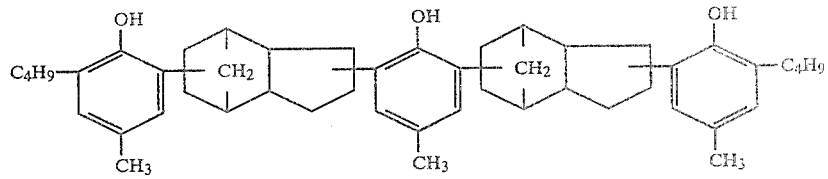

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertan, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids many if desired have inert, nonreactive substituents such as halogen, hydroxyl, alkyl radicals, alkenyl radicals and other carbocyclic ring structures condensed therewith. The oxygen-containing hetero-cyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chloroaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophosphites.

The organic triphosphites in which the radicals are monovalent radicals can be defined by the formula:

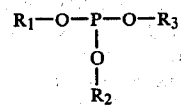

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two or $R_1$, $R_2$ and $R_3$ is hydrogen or a cation of a metal or ammonium.

Also included are the organic triphosphites having a bivalent organic radical forming a heterocyclic ring with the phosphorus of the type:

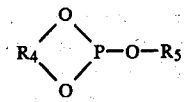

in which $R_4$ is a bivalent oganic radical selected from the group consisting of alkylene, arylene, aralkylene, alkarylene and cycloalkylene radicals having from two to about thirty carbon atoms, and $R_5$ is a monovalent oganic radical as defined above in the case of $R_1$, $R_2$ and $R_3$;

$R_5$ is hydrogen or a cation, in the case of the acid phosphites.

Also useful organic triphosphites are mixed heterocyclic-open chain phosphites of the type:

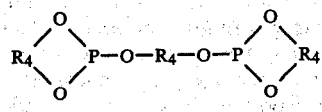

More complex triphosphites are formed from trivalent organic radicals, of the type:

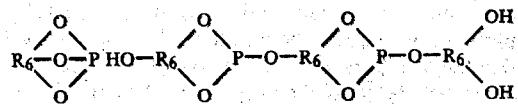

in which $R_6$ is a trivalent oganic radical of any of the types of $R_1$ to $R_5$, inclusive, as defined above.

A particularly useful class of complex triphosphites are the tetraoxadiphosphaspiro undecanes of the formula:

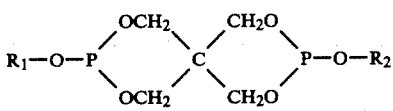

where

R₁ and R₂ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of R₁ and R₂ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

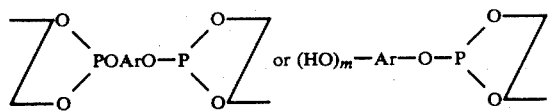

in which

Ar is a mono or bicyclic aromatic nucleus and m is an integer of from 0 to about 5. Z is one or a plurality of organic radicals as defined above for R₁ to R₆, taken singly or together in sufficient number to satisfy the valences of the two phosphite oxygen atoms.

One or both Z radicals is also hydrogen, in the case of the acid phosphites, and can include additional bicyclic aromatic groups of the type (HO)ₘ—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctylmonotolyl phosphite, tri-2-ethylhexyl phosphite, phenyl dicyclohexyl phosphite, phenyl diethyl phosphite, triphenyl phosphite, tricresyl phosphite, tri(dimethylphenyl) phosphite, trioctadecyl phosphite, triisooctyl phosphite, tridodecyl phosphite, isooctyl diphenyl phosphite, diisooctyl phenyl phosphite, tri(t-octylphenyl) phosphite, tri-(t-nonylphenyl) phosphite, benzyl methyl isopropyl phosphite, butyl dicresyl phosphite, isooctyl di(octylphenyl) phosphite, di(2-ethylhexyl) (isooctylphenyl) phosphite, tri-(2-cyclohxylphenyl) phosphite), tri-α-naphthyl phosphite, tri-(phenylphenyl) phosphite, tri(2-phenylethyl) phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and -cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro (5,5)-undecane, 3,9-di-(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di (methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy) ethyloxy group has an average molecular weight of 350),3,9-di(methoxy(polyethoxy) ethyloxy)-2,4,8,10-tetraoxa-3,9-diphosphaspiro-(5,5)-undecane (where the (polyethoxy) ethyloxy group has an average molecular weight of 550).

Exemplary of the bis aryl triphosphites are: bis (4,4'-thio-bis(2-tertiary-butyl-5-methyl-phenol))isooctyl phosphite, mono(4,4'-thio-bis(2-tertiary-butyl-5-methyl-phenol))di-phenyl phosphite, tri-(4,4'-n-butylidene-bis(2-tertiary-butyl-5-methyl-phenol)) phosphite, (4,4'-benzylidene-bis(2-tertiary-butyl-5-methyl-phenol)) diphenyl phosphite, isooctyl 2,2'-bis(-para-hydroxyphenyl) propane phosphite, decyl 4,4'-n-butylidene-bis(2-tertiary-butyl-5-methylphenol) phosphite, tri-4,4'-thio-bis(2-tertiary-butyl-5-methylphenol) phosphite, 2-ethylhexyl-2,2'-methylene-bis(4-methyl-6,1'-methylcyclohexyl) phenol phosphite, tri(2,2'-bis-(para-hydroxyphenyl) propane) phosphite, tri(4,4'-thio-bis(2-tertiary-butyl-5-methyl-phenol) phosphite, isooctyl-(2,6-bis(2'-hydroxy-3,5-dinonylbenzyl)-4-nonyl phenyl)) phosphite, tetra-tridecyl-4,4'-n-butylidene-bis(2-tertiary-butyl-5-methylphenyl) diphosphite, tetra-isooctyl-4,4'-thio-bis(2-tertiary-butyl-5-methylphenyl) diphosphite, 2,2'-methylene-bis(4-methyl-6,1'-methyl cyclohexyl phenyl) polyphosphite, isooctyl-4,4'-isopropylidene-bis-phenyl polyphosphite, 2-ethylhexyl-2,2'-methylene-bis(4-methyl-6,1'-methyl-cyclohexyl) phenyl triphosphite, tetra-tridecyl-4,4'-oxydiphenyl diphosphite, tetra-n-dodecyl-4,4'-n-butylidene bis (2-tertiary-butyl-5-methylphenyl) diphosphite, tetra-tridecyl-4,4'-isopropylidene bisphenyl diphosphite, hexa-tridecyl butane-1,1,3-tris(2'-methyl-5'-tertiary-butylphenyl-4') triphosphite.

Exemplary acid phosphites are di(phenyl) phosphite, monophenyl phosphite, mono(diphenyl phosphite, dicresyl phosphite, di-(o-isooctylphenyl) phosphite, di(p-ethylhexylphenyl) phosphite, di(p-t-octylphenyl) phosphite, di(dimethylphenyl) phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl) phosphite, monocyclohexyl phosphite, dicyclohexyl phosphite, di(2-cyclohexyl phenyl) phosphite, di-α-naphthyl phosphite, diphenyl phenyl phosphite, di(diphenyl) phosphite, di-(2-phenyl ethyl) phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-teriary-butyl-5-methylphenol)) phosphite, (4,4'-thio-bis(2-tertiary-butyl-5-methylphenol)) phenyl phosphite, bis(4,4'-n-butylidene-bis(2-tertiary-butyl-5-methylphenol)) phosphite, mono(4,4'-benzylidene-bis(2-tertiary-butyl-5-methylphenol)) phosphite, mono(2,2'-bis-(parahydroxyphenyl) propane) phosphite, mono(4,4'-butylidene-bis(2-tertiary-butyl-5-methylphenol) phosphite, bis(4,4'-thio-bis(2-tertiary-butyl-5-methylphenol)) phosphite, mono-2-ethylhexyl-mono-2,2'-methylene-bis(4-methyl-6,1'-methylcyclohexyl) phenol phosphite, bis(2,2'-bis(para-hydroxyphenyl)propane) phosphite, monoisooctylmono(4,4'-thio-bis(2-tertiary-butyl-5-methylphenol)) phosphite, isooctyl-(2,6-bis(2'-hydroxy-3,5-dinonylbenzyl)-4-nonylphenyl)) phosphite, tri-tridecyl-4,4'-n-butylidene-bis(2-tertiary-butyl-5-methylphenyl) diphosphite, triisooctyl-4,4'-thio-bis(2-tertiary-butyl-5-methylphenyl) diphosphite, bis(2,2'-methylene-bis(4-methyl-6,1'-methyl cyclohexyl phenyl)) phosphite, isooctyl-4,4'-isopropylidene-bis-phenyl phosphite, monophenyl mono(2,2'-methylene-bis(4-methyl-6,1'-methyl-cyclohexyl)) triphosphite, di-tridecyl-4,4'-oxydiphenyl diphosphite, di-n-dodecyl-4,4'-n-butylidene-bis(2-tertiary-butyl-5-methylphenyl) diphosphite, di-tridecyl-4,4'-isopropylidene bisphenyl diphosphite, tetra-tridecyl butane-1,1,3-tris(2'-methyl-5-tertiary-butylphenyl-4)-triphosphite.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl) benzotriazoles, 2(2-hydroxy-3-t-butyl-5-methylphenyl)-5-chlorobenzotriazole, 2(2-hydroxy-3-5-di-t-butylphenyl)-5-chlorobenzotriazole, 2(2-hydroxy-3,5-di-t-amylphenyl) benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-octyl-phenolate), nickel-monoethyl(3,5-di-t-butyl-4-hydroxybenzyl) phosphonate, substituted acrylonitriles such as methyl-α-cyano-β-methyl-β-(p-methoxy phenyl) acrylate and oxalic anilides such a N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 10% total stabilizers including the alkyl thiopropionyl hydrazino triazines of the invention by weight of the polymer are satisfactory. Preferably, from 0.01 to 5% is employed for optimum stabilization.

The stabilizer systems of the invention are readily rendered in solid particulate form, comprising a blend of:

(a) alkyl thiopropionyl hydrazino triazine stabilizer in an amount of from about 10 to about 35 parts by weight;

and optionally:

(b) a phenolic antioxidant in an amount from about 10 to about 35 parts by weight; and/or (c) other heat or light stabilizers in an amount of from about 10 to about 35 parts by weight.

The alkyl thiopropionyl hydrazino triazine stabilizers of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples in the opinion of the inventors represent preferred embodiments of synthetic resin compositions containing the alkyl thiopropionyl hydrazino triazine stabilizers of the invention.

EXAMPLES 1 to 10

Polypropylene compositions were prepared using stabilizers of the invention and of the prior art, and having the following formulation:

| Ingredient | Parts by Weight |
| --- | --- |
| Polypropylene | 100 |
| Calcium stearate | 0.2 |
| Stearyl-β-(3,5-di-t-butyl-4-hydroxyphenyl propionate | 0.1 |
| Stabilizer as shown in Table I | 0.2 |

The compositions were thoroughly blended and then extruded (cylinder temperature 230° and 240° C., head die temperature 250° C., velocity 20 rpm). Test pieces of 95×40×1 mm were then injection-molded at 250° C.

The test pieces were heated in a Geer oven at 170° C. to evaluate heat stability. The hours to failure were noted, and are shown in Table I.

TABLE I

| Example No. | Stabilizer | Hours to Failure |
|---|---|---|
| Control 1 | Dilaurylthiodipropionate | 280 |
| Control 2 | Bis(dodecylthiopropionyl) hydrazine | 240 |
| Example 1 | Triazine with three $-NHNHCOC_2H_4SC_{12}H_{25}$ substituents | 480 |
| Example 2 | Triazine with $N(C_4H_9)_2$ and two $-NHNHCOC_2H_4SC_{12}H_{25}$ substituents | 430 |
| Example 3 | Triazine with 2,2,6,6-tetramethylpiperidin-4-ylamino and two $-NHNHCOC_2H_4SC_{12}H_{25}$ substituents | 420 |
| Example 4 | Bis-triazine bridged by $-NH-C_6H_{12}-NH-$, each triazine bearing two $-NHNHCOC_2H_4SC_{12}H_{25}$ groups | 450 |
| Example 5 | Bis-triazine bridged by $-NHNH-$, each triazine bearing two $-NHNHCOC_2H_4SC_8H_{17}$ groups | 430 |
| Example 6 | Bis-triazine bridged by $-NHNHCOC_{10}H_{20}CONHNH-$, each triazine bearing two $-NHNHCOC_2H_4SC_{18}H_{37}$ groups | 440 |

TABLE I-continued

| Example No. | Stabilizer | Hours to Failure |
|---|---|---|
| Example 7 | (structure: triazine dimer with NHNHCC₂H₄SC₁₂H₂₅ substituents) | 470 |
| Example 8 | (structure: [triazine]₅ oligomer bridged by NHC₆H₁₂NH with NHNHCC₂H₄SC₁₂H₂₅ substituents) | 390 |
| Example 9 | (structure: [triazine]₃ oligomer bridged by NHNHC(O)C(O)NHNH with NHNHCC₂H₄SC₁₂H₂₅ substituents) | 450 |
| Example 10 | (structure: [triazine]₅ oligomer bridged by NH-C₁₁H₂₂-NH with NHNHCC₂H₄SC₁₄H₂₉ substituents, terminated by H₂NC₁₁H₂₂-NH) | 410 |

The superiority of the alkyl thiopropionyl hydrazinyl triazines of the invention to the prior art compounds is evident from the data.

EXAMPLES 11 to 18

High density polyethylene compositions were prepared, using stabilizers of the invention and of the prior art, and having the following formulation:

| Ingredient | Parts by Weight |
|---|---|
| High-density polyethylene | 100 |
| Stearyl-β-(3,5-di-t-butyl-4-hydroxyphenyl)propionate | 0.1 |
| Stabilizer as shown in Table II | 0.3 |

The stabilizer was blended with the polymer on a two-roll mill and sheets 1.0 mm thick were prepared by compression molding of the blend. Pieces of 10×20 mm were cut off from the sheets and heated in a Geer oven at 150° C. on aluminum foil to evaluate heat stability. The time in hours when degradation set in, as determined by a significant discoloration and/or embrittlement, was noted as hours to failure. The results are reported in Table II.

TABLE II

| Example No. | Stabilizer | Hours to Failure |
|---|---|---|
| Control 1 | Dilaurylthiodipropionate | 350 |
| Control 2 | Bis(dodecylthiopropionyl) hydrazine | 330 |

TABLE II-continued
| Example No. | Stabilizer | Hours to Failure |
|---|---|---|
| Example 11 | 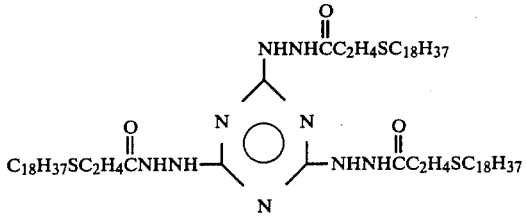 | 520 |
| Example 12 | 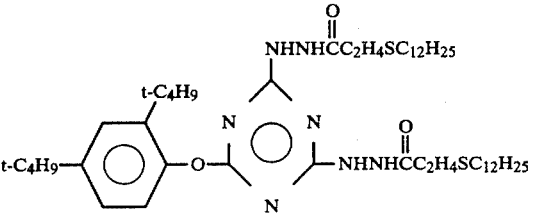 | 460 |
| Example 13 | 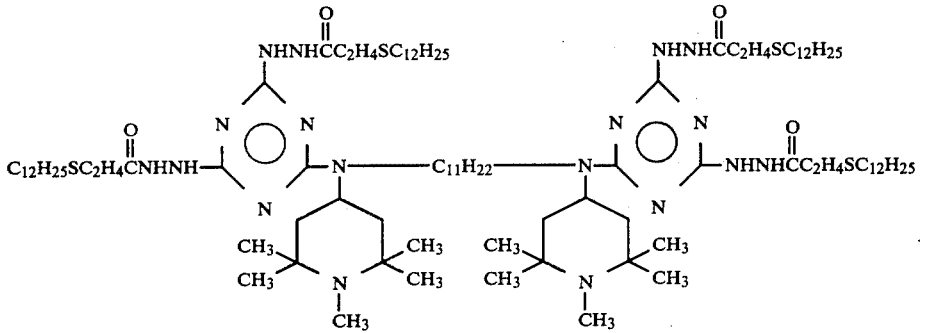 | 470 |
| Example 14 | 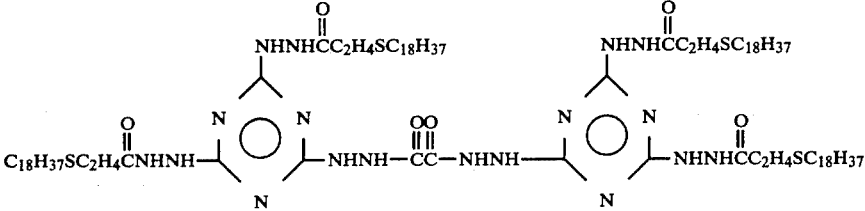 | 500 |
| Example 15 | 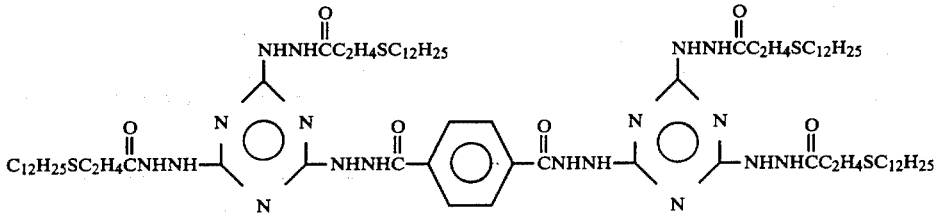 | 450 |
| Example 16 | 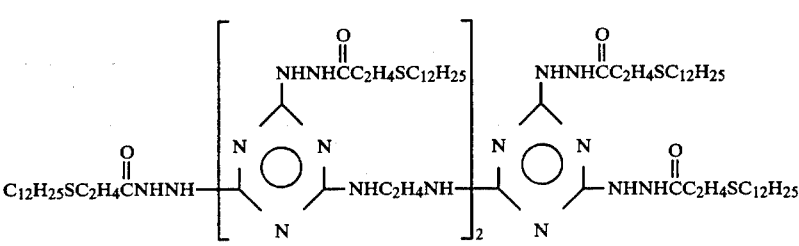 | 460 |

TABLE II-continued

| Example No. | Stabilizer | Hours to Failure |
|---|---|---|
| Example 17 | 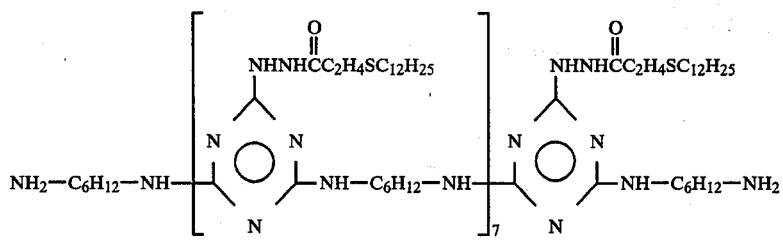 | 450 |
| Example 18 | 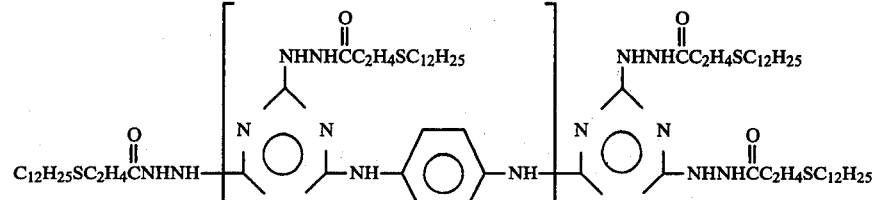 | 490 |

The superiority of the alkyl thiopropionyl hydrazinyl triazines of the invention to the prior art compounds is evident from the data.

EXAMPLES 19 to 25

Acrylonitrile-butadiene-styrene terpolymer resin compositions were prepared using stabilizers of the invention and of the prior art, and having the following formulation:

| Ingredient | Parts by Weight |
|---|---|
| ABS resin | 100 |
| Calcium stearate | 1.0 |
| 1,3,5-Tris(3,5-di-t-butyl-4- hydroxybenzyl isocyanurate | 0.1 |
| Stabilizer as shown in Table III | 0.2 |

The stabilizers were blended with the resin and extruded at 200° C., followed by injection-molding at 230° C. of the resulting blend to prepare samples 1 mm thick. Heat stability was evaluated by heating the specimen samples at 135° C. in a Geer oven for thirty hours. The whiteness of the specimens was evaluated using a Hunter color difference meter. Izod impact strength of the specimens was determined at 20° C. The results are shown in Table III.

TABLE III

| Example No. | Stabilizer | Whiteness | Izod impact strength (Kg · cm/cm) Original | After heating |
|---|---|---|---|---|
| Control 1 | None | 14.3 | 17.3 | 10.8 |
| Control 2 | Dilaurylthiodipropionate | 17.1 | 17.7 | 13.2 |
| Control 3 | Bis(dodecylthiopropionyl)hydrazine | 20.6 | 18.0 | 15.4 |
| Example 19 | 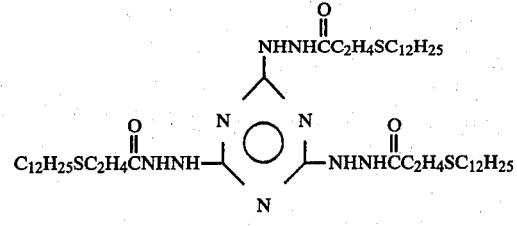 | 35.8 | 18.3 | 17.4 |
| Example 20 | 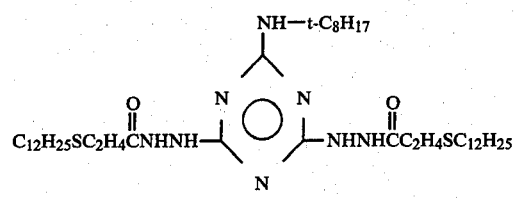 | 32.5 | 18.2 | 17.1 |
| Example 21 |  | 31.6 | 18.5 | 17.3 |

TABLE III-continued

| Example No. | Stabilizer | Whiteness | Izod impact strength (Kg · cm/cm) Original | After heating |
|---|---|---|---|---|
| Example 22 | [structure: triazine dimer linked by NH—C$_6$H$_{12}$—NH with NHNHCOC$_2$H$_4$SC$_{12}$H$_{25}$ substituents] | 33.8 | 18.3 | 17.2 |
| Example 23 | [structure: triazine dimer linked by NHNH—COCO—NHNH with NHNHCOC$_2$H$_4$SC$_{18}$H$_{37}$ substituents] | 29.4 | 18.0 | 16.8 |
| Example 24 | [structure: triazine dimer linked by O—CH$_2$—C(CH$_3$)$_2$—CH$_2$—O with NHNHCOC$_2$H$_4$SC$_{12}$H$_{25}$ substituents] | 30.9 | 18.2 | 17.2 |
| Example 25 | [structure: triazine with piperidine groups linked by C$_6$H$_{12}$ with NHNHCOC$_2$H$_4$SC$_{12}$H$_{25}$ substituents] | 30.7 | 18.1 | 17.0 |
| | [structure: triazine dimer linked by NHNHCOC$_{10}$H$_{20}$CONHNH with NHNHCOC$_2$H$_4$SC$_{12}$H$_{25}$ substituents] | | | |

The superiority of the alkyl thiopropionyl hydrazinyl triazines of the invention to the prior art compounds is evident from the data.

EXAMPLES 26 to 33

Talc-filled polypropylene compositions were prepared using stabilizers of the invention and of the prior art, and having the following formulation:

| Ingredient | Parts by Weight |
|---|---|
| Polypropylene | 100 |
| Talc | 40 |
| Tetrakis[methylene-(3,5-di-t-butyl-4-hydroxyphenyl propionate] methane | 0.1 |
| Calcium stearate | 0.2 |

| -continued | |
|---|---|
| Ingredient | Parts by Weight |
| Stabilizer as Shown in Table IV | 0.2 |

The stabilizer was blended with the polymer and extruded, followed by injection-molding at 250° C. of the resulting blend, to prepare samples 1 mm thick.

Heat stability was evaluated by heating the specimen samples at 160° C. in a Geer oven. Elongation of the specimens was determined before and after heating the specimens at 150° C. in a Geer oven for 7 days. The results are shown in Table IV.

TABLE IV

| Example No. | Stabilizer | Hours to failure | Elongation (%) Original | Elongation (%) After heating |
|---|---|---|---|---|
| Control 1 | Dilaurylthiodipropionate | 240 | 41.3 | 30.7 |
| Control 2 | Bis(dodecylthiopropionyl)hydrazine | 290 | 45.5 | 36.2 |
| Example 26 | triazine ring with three $-NHNHCOC_2H_4SC_{12}H_{25}$ substituents | 520 | 83.0 | 68.9 |
| Example 27 | triazine ring with three $-NHNHCOC_2H_4SC_{18}H_{37}$ substituents | 500 | 77.4 | 63.5 |
| Example 28 | bis-triazine bridged by $-NHNH-$ with four $-NHNHCOC_2H_4SC_8H_{17}$ substituents | 460 | 73.1 | 59.2 |
| Example 29 | bis-triazine bridged by $-NHNH-COCO-NHNH-$ with four $-NHNHCOC_2H_4SC_{18}H_{37}$ substituents | 520 | 80.6 | 66.4 |
| Example 30 | bis-triazine bridged by $-NHNHCOC_2H_4SC_2H_4CONHNH-$ with four $-NHNHCOC_2H_4SC_{12}H_{25}$ substituents | 510 | 81.4 | 67.0 |
| Example 31 | | 450 | 75.7 | 62.6 |

TABLE IV-continued

| Example No. | Stabilizer | Hours to failure | Elongation (%) Original | Elongation (%) After heating |
|---|---|---|---|---|
| Example 32 | (structure shown) | 480 | 74.8 | 63.8 |
| Example 33 | (structure shown) | 470 | 78.3 | 65.7 |
|  | (structure shown) |  |  |  |

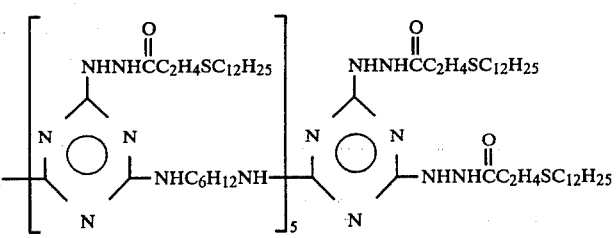

The superiority of the alkyl thiopropionyl hydrazinyl triazines of the invention to the prior art compounds is evident from the data.

EXAMPLES 34 to 40

High density polyethylene compositions comprising fine copper powder were prepared using stabilizers of the invention and of the prior art, and having the following formulation:

| Ingredient | Parts by Weight |
|---|---|
| High density polyethylene | 100 |
| Fine copper powder | 1.2 |
| Stabilizer as shown in Table V | 0.2 |

The stabilizer was blended with the polymer on a two-roll mill and sheets 0.5 mm thick were prepared by compression molding of the blend at 150° C. and 200 kg/cm².

Pieces 2.5 cm square were cut off from the sheets, and heated in a Geer oven at 150° C. to evaluate heat stability. The hours to failure were noted, and the results are shown in Table V.

TABLE V

| Example No. | Stabilizer | Hours to Failure |
|---|---|---|
| Control 1 | None | 20 |
| Control 2 | Bis(dodecylthiopropionyl)hydrazine | 180 |
| Example 34 | (structure shown) | 360 |

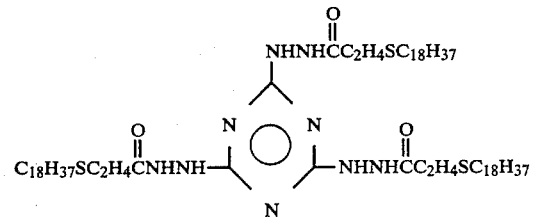

TABLE V-continued

| Example No. | Stabilizer | Hours to Failure |
|---|---|---|
| Example 35 | [structure: triazine with NH-t-$C_8H_{17}$ and two $C_{12}H_{25}SC_2H_4C(O)NHNH$- groups] | 320 |
| Example 36 | [structure: bis-triazine bridged by -NHNH-, with $C_8H_{17}SC_2H_4C(O)NHNH$- substituents] | 350 |
| Example 37 | [structure: two triazines bridged by -NHNHC(O)-C$_6$H$_4$-C(O)NHNH-, with $C_{12}H_{25}SC_2H_4C(O)NHNH$- substituents] | 310 |
| Example 38 | [structure: oligomer, $[...\text{triazine}-NHC_6H_{12}NH...]_5$ with $C_{12}H_{25}SC_2H_4C(O)NHNH$- end groups] | 310 |
| Example 39 | [structure: oligomer, $[...\text{triazine}-NHNHC(O)-C(O)NHNH...]_3$ with $C_{12}H_{25}SC_2H_4C(O)NHNH$- end groups] | 330 |
| Example 40 | [structure: oligomer, $[...\text{triazine}-NHNHC(O)C_{10}H_{20}C(O)NHNH...]_2$ with $C_{12}H_{25}SC_2H_4C(O)NHNH$- end groups] | 370 |

The superiority of the alkyl thiopropionyl hydrazinyl triazines of the invention to the prior art compounds is evident from the data.

EXAMPLES 41 to 48

Polypropylene compositions comprising a hindered piperidinyl amine compound were prepared using the stabilizer of this invention and stabilizers of the prior art, and having the following formulation:

| Ingredient | Parts by Weight |
|---|---|
| Polypropylene | 100 |
| Tetrakis[methylene-(3,5-di-t-butyl-4-hydroxyphenyl)propionate] methane | 0.1 |
| Bis(2,2,(6,6-tetramethyl-4-piperidinyl) sebacate | 0.15 |

-continued

| Ingredient | Parts by Weight |
|---|---|
| Stabilizer as shown in Table VI | 0.2 |

The test pieces were prepared as in Examples 1 to 10. The heat stability of the pieces were evaluated by heating in a Geer oven at 160° C. The test pieces were exposed to a high voltage mercury lamp to determine the light stability. The results are shown in Table VI.

TABLE VI

| Example No. | Stabilizer | Heat Stability (hrs) | Light Stability (hrs) |
|---|---|---|---|
| Control 1 | None | 300 | 310 |
| Control 2 | Dilaurylthiodipropionate | 460 | 140 |
| Control 3 | Bis(dodecylthiopropionyl)hydrazine | 680 | 380 |
| Example 41 | [structure] | 1,170 | 720 |
| Example 42 | [structure] | 940 | 650 |
| Example 43 | [structure] | 980 | 680 |
| Example 44 | [structure] | 1,010 | 740 |
| Example 45 | [structure] | 1,120 | 680 |

TABLE VI-continued

| Example No. | Stabilizer | Heat Stability (hrs) | Light Stability (hrs) |
|---|---|---|---|
| Example 46 | | 1,030 | 660 |
| Example 47 | | 1,060 | 730 |
| Example 48 | | 920 | 610 |

The superiority of the alkyl thiopropionyl hydrazinyl triazines of the invention to the prior art compounds is evident from the data.

Having regard to the foregoing disclosure, the following is claimed as inventive and patentable embodiments thereof:

1. Alkyl thiopropionyl hydrazino triazines having the formula:

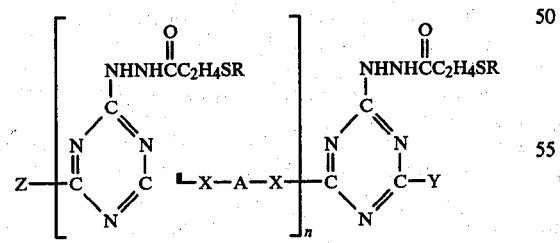

wherein:
R is alkyl having from one to about fifty carbon atoms;
X is

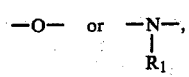

where $R_1$ is selected from the group consisting of hydrogen, alkyl having from one to about fifty carbon atoms; and

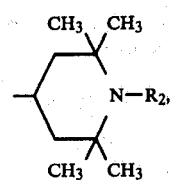

where $R_2$ is selected from the group consisting of hydrogen, O and alkyl hydroxyalkyl, epoxy alkyl and acyloxy alkyl having from one or two to about eight carbon atoms;
when X is O, A is selected from the group consisting of alkylene having from two to about twenty carbon atoms, cycloalkylene having from about five to about eight carbon atoms and phenylene;
when X is

A is selected from the group consisting of a direct linkage, alkylene having from one to about twenty carbon atoms, cycloalkylene having from five to about eight carbon atoms; phenylene; and

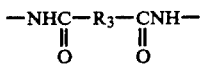

where R₃ is selected from the group consisting of a direct linkage, alkylene having from one to about twenty carbon atoms; cycloalkylene having from about five to about eight carbon atoms; phenylene; and thiodialkylene having from about two to about twenty carbon atoms;

Y and Z are each selected from the group consisting of

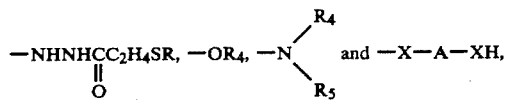

where R₄ and R₅ each are selected from the group consisting of hydrogen; alkyl having from one to about fifty carbon atoms, cycloalkyl having from about five to about eight carbon atoms; phenyl; and alkyl phenyl having from seven to about twenty carbon atoms; and

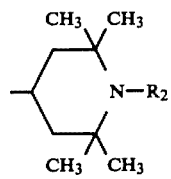

n is a number from 0 to about 20.

2. Alkyl thiopropionyl hydrazino triazines according to claim 1 in which X is O.

3. Alkyl thiopropionyl hydrazino triazines according to claim 1 in which X is

4. Alkyl thiopropionyl hydrazino triazines according to claim 3 in which R₁ is

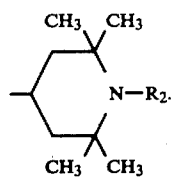

5. Alkyl thiopropionyl hydrazino triazines according to claim 1 in which X is O and A is alkylene.

6. Alkyl thiopropionyl hydrazino triazines according to claim 1 in which X is O and A is cycloalkylene.

7. Alkyl thiopropionyl hydrazino triazines according to claim 1 in which X is O and A is phenylene.

8. Alkyl thiopropionyl hydrazino triazines according to claim 1 in which X is

and A is alkylene.

9. Alkyl thiopropionyl hydrazino triazines according to claim 1 in which X is

and A is cycloalkylene.

10. Alkyl thiopropionyl hydrazino triazines according to claim 1 in which X is

and A is phenylene.

11. Alkyl thiopropionyl hydrazino triazines according to claim 1 in which X is

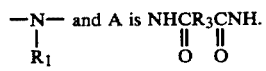

12. Alkyl thiopropionyl hydrazino triazines according to claim 1 in which X is

and A is a direct linkage.

13. Alkyl thiopropionyl hydrazino triazines according to claim 1 in which Y and Z are each

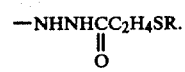

14. Alkyl thiopropionyl hydrazino triazines according to claim 1 in which Y and Z are each —OR.

15. Alkyl thiopropionyl hydrazino triazines according to claim 1 in which Y and Z are each

16. Alkyl thiopropionyl hydrazino triazines according to claim 1 in which Y and Z are each —X—A—XH.

17. Alkyl thiopropionyl hydrazino triazines according to claim 1 in which n is 0.

18. Alkyl thiopropionyl hydrazino triazines according to claim 1 in which n is 1.

19. Alkyl thiopropionyl hydrazino triazines according to claim 1 in which n is 2.

20. An olefin polymer composition having improved resistance to deterioration upon exposure to light comprising an olefin polymer selected from the group consisting of polymers of alpha-olefins having from two to six carbon atoms and polystyrene, and a compound in accordance with claim 1.

21. An olefin polymer composition in accordance with claim 20 wherein the polyolefin is polypropylene.

22. An olefin polymer composition in accordance with claim 20 wherein the polyolefin is polyethylene.

23. An olefin polymer composition in accordance with claim 20 wherein the polyolefin is ethylene-propylene copolymer.

24. An acrylonitrile-butadiene-styrene polymer having improved resistance to deterioration upon exposure to light comprising an acrylonitrile-butadiene-styrene polymer and a compound in accordance with claim 1.

* * * * *